United States Patent [19]

DeHaven-Hudkins et al.

[11] Patent Number: 5,364,867
[45] Date of Patent: Nov. 15, 1994

[54] 4-PHENYLPIPERDINE AGENTS FOR TREATING CNS DISORDERS

[75] Inventors: Diane L. DeHaven-Hudkins, Township of Uwchlan, Pa.; John P. Mallamo, Town of Kinderhook; William F. Michne, Town of Poestenkill, both of N.Y.

[73] Assignee: Sterling Winthrop Inc., New York, N.Y.

[21] Appl. No.: 982,922

[22] Filed: Nov. 30, 1992

[51] Int. Cl.$^5$ .................. A61K 31/445; C07D 211/32; C07D 401/02
[52] U.S. Cl. ..................... 514/326; 514/212; 514/316; 514/317; 514/327; 514/330; 540/590; 546/189; 546/208; 546/217; 546/225; 546/227; 546/236; 546/240
[58] Field of Search ................. 540/597; 546/189, 208, 546/217, 218, 225, 228, 236, 240; 514/212, 326, 327, 330, 331

[56] References Cited

U.S. PATENT DOCUMENTS

| | | | |
|---|---|---|---|
| 2,486,794 | 11/1949 | Miescher et al. | 546/215 |
| 2,880,211 | 3/1959 | Elpern | 546/218 |
| 2,898,340 | 8/1959 | Janssen | 546/228 |
| 2,914,532 | 11/1959 | Elpern | 546/228 |
| 2,951,080 | 8/1960 | Pohland | 546/228 |
| 2,960,507 | 11/1960 | Stern and Lawson | 546/214 |
| 3,024,234 | 3/1962 | Stern | 544/130 |
| 3,043,844 | 7/1962 | Elpern | 546/225 |
| 3,080,372 | 3/1963 | Janssen | 546/225 |
| 3,141,021 | 7/1964 | Janssen | 546/217 |
| 3,209,006 | 9/1965 | Wragg et al. | 546/229 |
| 3,217,009 | 11/1965 | Carabateas | 546/218 |
| 3,539,580 | 11/1970 | Hermans and Verhoeven | 546/217 |
| 3,627,772 | 12/1971 | Freter et al. | 546/228 |
| 3,674,799 | 7/1972 | Edenhofer and Spiegelberg | 546/334 |
| 3,708,597 | 1/1973 | Merz et al. | 546/225 |
| 4,022,786 | 5/1977 | Hackmack and Klosa | 546/192 |
| 4,929,734 | 5/1990 | Coughenour | 546/338 |
| 5,206,249 | 4/1993 | Smith | 514/289 |

FOREIGN PATENT DOCUMENTS 75024317 8/1975 Japan.
931789 3/1960 United Kingdom ............ 546/226

OTHER PUBLICATIONS

Leander, J. D. & D. M. Zimmerman, "Antagonism of Bremazocine-Induced Urinaation as a Test for Kappa-Opioid Receptor Antagonists within the Phenylpiperidine Series" *Drug Devel. Res.* 4:421–427 (1984).

Glennon, R. A. et al., "Novel 1-Phenylpiperazine and 4-Phenylpiperidine Derivatives as High-Affinity Sigma Ligands", *J. Med. Chem.* 34:3360–3365 (1991).

*Primary Examiner*—Celia Chang
*Attorney, Agent, or Firm*—Richard A. Hake; Paul E. DuPont

[57] ABSTRACT

4-Phenylpiperidines of the formula

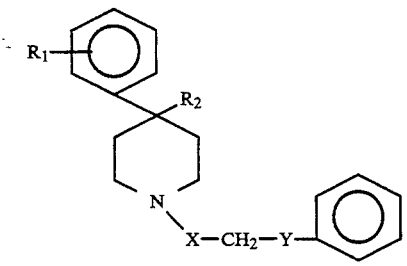

wherein
  $R_1$ is hydrogen, hydroxy or lower-alkoxy;
  $R_2$ is hydrogen, hydroxy, lower-alkanoyl, aroyl, lower-alkoxycarbonyl, lower-alkanoyloxy, lower-alkoxycarbonyl, or $CONR_3R_4$; $R_3$ and $R_4$ are the same or different lower-alkyl or $R_3$ and $R_4$ together represent a lower-alkylene chain;
  X is methylene or carbonyl;
  Y is methylene, C=NOH, hydroxymethylene or carbonyl;

or pharmaceutically acceptable acid addition salts thereof, are useful in the treatment of psychoses and other ailments of the central nervous system.

16 Claims, No Drawings

4-PHENYLPIPERDINE AGENTS FOR TREATING CNS DISORDERS

BACKGROUND OF THE INVENTION

1. Field of the Invention

This invention relates to 4-phenylpiperidines which are useful in the treatment of disorders of the central nervous system, and to pharmaceutical compositions thereof and methods for use thereof as central nervous system disorder treatments.

A number of known antipsychotic drugs are disclosed in the art which have been shown to share a selective, high affinity for sigma receptors, which are sites where psychotomimetic opiates such as (+)-pentazocine and N-allylnormetazocine act. It has been suggested that the antipsychotic behavioral profile of these antipsychotic drugs can be attributed to their role as competitive antagonists of sigma receptor binding and that a systematic screen for drugs that block sigma receptors may provide a valuable strategy for identifying novel antipsychotic agents. Additionally, it has been shown that the relative potencies of these agents studied in vivo correspond well with their relative binding affinities obtained in vitro. See, for example, Snyder and Largent, J. Neuropsychiatry 1989, 1(1), 7–15; Largent et al., Clinical Neuropharmacology 1988, 11(2), 105–119; Taylor et al., Drug Development Research 1987, 11, 65–70; Ferris et al., Life Sciences 1986, 38(25), 2329–2337; and Su et al., Neuroscience Letters 1986, 71, 224–228.

The common property of neuroleptic drugs as sigma receptor ligands suggests that sigma interactions mediate some of the antipsychotic effects of neuroleptics. The distribution of sigma receptors in the limbic areas known to be involved in cognition and emotion supports this view.

2. Information Disclosure Statement

Piperidines having a wide variety of substituents attached to the 4-position carbon atom of the piperidine ring are known in the art. Such substituted-piperidines are also known in which one or more lower-aliphatic hydrocarbon radicals are attached to other carbon atoms of the piperidine ring. Piperidines so substituted are known having various radicals attached to the nitrogen atom of the piperidine ring, such as lower-alkyl, aralkyl, aralkenyl, aryloxyalkyl and arylmercaptoalkyl.

Miescher et al. U.S. Pat. No. 2,486,794 (issued Nov. 1, 1949) discloses compounds having the formula:

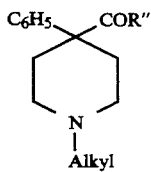

where R″ is a hydrocarbon radical, specifically methyl or ethyl and processes for the preparation thereof.

Elpern U.S. Pat. No. 2,880,211 (issued Mar. 31, 1959) discloses compounds having the formula

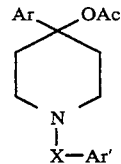

where Ar is an aryl radical of the benzene or naphthylene series, Ar′ is an aryl radical of the benzene series, Ac is a lower carboxylic acyl radical and X is a divalent aliphatic hydrocarbon radical of 2–6 carbon atoms. These compounds are said to be useful as analgesics.

Janssen U.S. Pat. No. 2,898,340 (issued Aug. 4, 1959) discloses compounds having the formula:

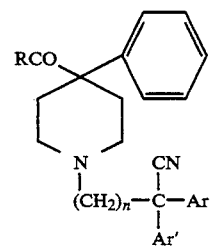

where Ar and Ar′ are aryl hydrocarbon radicals, preferably of less than nine carbon atoms, n is 2 or 3 and R is lower-alkyl, lower-alkoxy, lower-alkenyloxy, cycloalkyloxy or aryloxy. The compounds are said to be "highly active inhibitors of gastrointestinal propulsion and defecation and are therefore useful in the treatment of diarrhea".

Elpern U.S. Pat. No. 2,914,532 (issued Nov. 24, 1959) discloses lower-alkyl 4-phenyl-1-(hydrocarbonyl)-piperidine-4-carboxylates; in particular, lower-alkyl 4-phenyl-1-(3-phenylpropyl)piperidine-4-carboxylates, their acid addition salts, and the preparation of these compounds. Ethyl 1-(3-phenylpropyl)-4-phenyl-4-piperidinecarboxylate used in preparation of Example 2 is disclosed therein as Example 1. The compounds are stated to have analgesic activity.

Stern et al. U.S. Pat. Nos. 2,960,507 (issued Nov. 15, 1960) and 3,024,234 (patented Mar. 6, 1962) disclose compounds having the formula:

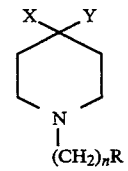

where X is phenyl; Y is hydroxy or an esterified hydroxy group, (for example acetoxy or propionoxy): R is alkoxy, aryloxy, aralkoxy or cycloalkoxy or "a heterocyclic residue containing an oxygen atom" and n is an integer from 2 to 6. The compounds are said to have analgesic properties and to depress the cough-reflex center.

Elpern U.S. Pat. No. 3,043,844 (issued Jul. 10, 1962) discloses compounds having the formula:

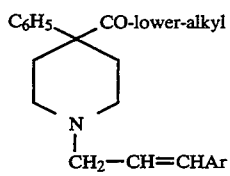

where Ar is a monocarbocyclic aryl radical having 6 ring carbons which are said to be useful as analgesics and antitussives.

Janssen U.S. Pat. No. 3,080,372 (issued Mar. 5, 1963) discloses compounds having the formula:

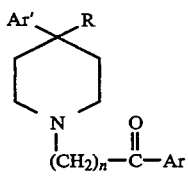

where Ar is phenyl, halophenyl, thienyl and anisyl; Ar' is phenyl, halophenyl, alkylphenyl, anisyl or trifluoromethylphenyl; R is hydrogen, lower-alkyl, hydroxy, lower-alkyl, CHO and lower-alkanoyl. The compounds are said to have CNS depressant activity.

Janssen U.S. Pat. No. 3,141,021 (patented Jul. 14, 1964) discloses compounds having the formula:

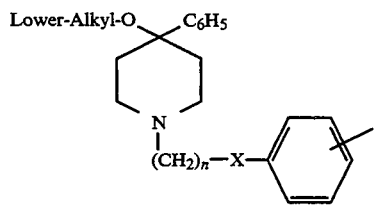

where Y is hydrogen, methyl, methoxy or fluorine; X is $CH_2$ or $CH=CH$; n is an integer less than 4; and lower-alkyl is methyl, ethyl, propyl or butyl. The compounds are said to be useful as anticonvulsants.

Wragg et al. U.S. Pat. No. 3,209,006 (patented Sep. 28, 1965) discloses compounds having the formula:

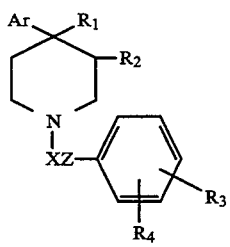

where X represents a straight, saturated or straight, monoethylenically unsaturated hydrocarbon chain of one of three carbon atoms; Z represents a —$CH_2$—, =CH—, —CO— or —CHOH— group, Ar represents a phenyl group substituted in the meta position by a substituent selected from chlorine, bromine and fluorine atoms and trifluoromethyl groups; $R_1$ and $R_2$ when taken separately represent hydrogen atoms or when taken together represent a single bond, $R_3$ is in one of the positions meta and para and is selected from hydrogen, amino, mono-alkylamino, dialkylamino, monohydroxyalkylamino, di(hydroxyalkyl) amino, lower aliphatic acyloxyalkylamino, lower aliphatic acylamido (including lower alkane sulphonamido), N-lower alkyl aliphatic acylamido, nitro, carbamoylamino, and alkoxycarbonylamino groups; and $R_4$ is in one of the positions meta and para and is hydrogen or an amino group. By the terms "lower", "alkyl", "alkoxy" and "hydroxyalkyl" as used throughout this specification and accompanying claims is meant alkyl, alkoxy, hydroxyalkyl and other groups containing up to 4 carbon atoms. The compounds are said to be useful as antihistaminics, hypothermic agents and local anesthetic potentiators and also to be "useful veterinary medicine".

Carabateas U.S. Pat. No. 3,217,009 (issued Nov. 9, 1965) discloses compounds having a molecular structure in which a lower-acyloxy substituent is attached to the remaining 4-position of 4-aryl-1-[ω-aromatic-ω-oxo-(lower-alkyl)]-piperidines. 4-Phenyl-1-(3-oximino-3-phenylpropyl)-4-propionoxypiperidine used as Example 7 in this specification is disclosed therein. Compounds are stated to be useful as analgesics.

Hermans et al. U.S. Pat. No. 3,539,580 (issued Nov. 10, 1970) discloses compounds having the formula:

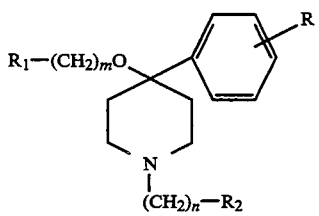

where R is hydrogen, lower-alkyl, halo or trifluoromethyl; $R_1$ is di-(lower-alkyl)amino, 1-piperidinyl or 1-azepinyl; $R_2$ is Z, Z—NH— or Z—NH—CO—, wherein Z is phenyl or phenyl mono or disubstituted by lower-alkyl or halo; and m and n are each 2 or 3. The compounds are said to be useful as local anesthetics.

Freter et al. U.S. Pat. No. 3,627,772 (issued Dec. 14, 1971) discloses compounds having the formula:

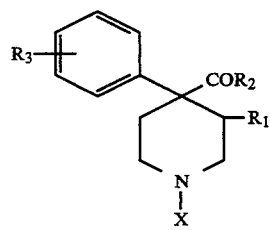

where $R_1$ is hydrogen or α or β-$CH_3$; $R_2$ is methyl, ethyl, n-propyl, methoxy, ethoxy or n-propoxy; $R_3$ is methyl, hydroxy, methoxy, acetoxy, fluorine, chlorine or bromine; and X is a variety of 1-(2-propenyl) groups substituted on the 1-, 2- or 3-carbon atoms by methyl, bromine or chlorine. The compounds are said to be useful as "morphine-antagonistic analgesics".

Edenhofer et al. U.S. Pat. No. 3,674,799 (issued Jul. 4, 1972) discloses compounds having the formula:

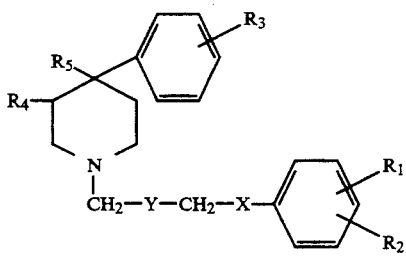

where R₁ is hydrogen, amino, lower-alkylamino, lower-alkanoylamido, aroylamido, N-(lower-alkyl)-lower-alkanoylamido, lower-alkyl-sulfonylamido, carbamoyl or ureido; R₂ is hydrogen, halogen, lower-alkyl or lower-alkoxy; R₃ is halogen; R₄ is hydrogen; R₅ is hydrogen or hydroxy; R₄ together with R₅ is a carbon-carbon bond; X is —O— or —S—; and Y is methylene, hydroxymethylene, lower-alkanoyl-oxymethylene, lower-alkylsulfonyloxymethylene, aryl-sulfonyloxymethylene or carbonyl. The compounds are said to be useful as antiphlogistic, antiallergic, antitussive or analgesic agents.

Merz et al. U.S. Pat. No. 3,708,597 (issued Jan. 2, 1973) discloses the compound

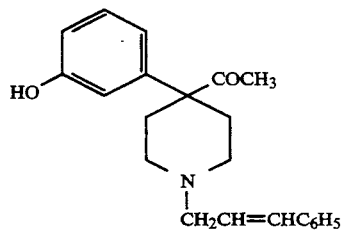

which is said to be useful as an analgesic.

Hackmack et al. U.S. Pat. No. 4,022,786 (issued May 10, 1977) and divisional thereof Menge et al. U.S. Pat. No. 4,016,280 (patented Apr. 5, 1977) disclose 4,4-diarylpiperidines having the formula:

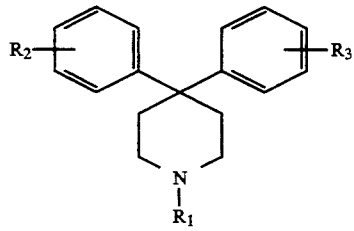

where R₁ is hydrogen, C₁₋₆ alkyl, substituted or unsubstituted phenyl-lower-alkyl, hydroxy-lower-alkyl, (lower) alkyl[carbonyl or oxo](loweralkyl), lower-alkoxy-lower-alkyl, substituted or unsubstituted phenyl-lower-alkoxy-lower-alkyl, said substituents "being a halogen atom having an atomic number from 9 to 35"; R₂ and R₃ are independently hydrogen or C₁₋₄ alkyl; R₄ is hydrogen or R₅ substituted benzoyl, where R₅ has the same meanings as R₂; and R₆ is halogen or hydroxy. The compounds are said to be useful as CNS stimulants.

Japanese Patent Publication 75/024317 (published Aug. 14, 1975) discloses compounds having the formula:

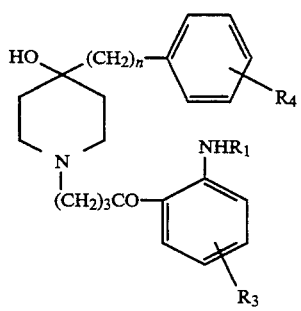

where R₁ is hydrogen or lower-alkyl; R₃ is hydrogen or halogen; R4 is hydrogen, halogen, lower-alkyl or trifluoromethyl; and n is 0 or 1. The compounds are said to be major tranquilizers with CNS depressant and analgisic activities.

Leander et al., Drug Dev. Res., 4(4), 421–7 (1984) discloses compounds having the formula:

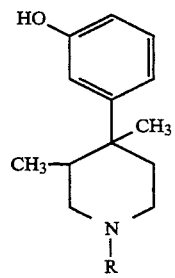

where R is methyl, phenylalkyl or allyl, which were studied for their kappa-opioid receptor antagonist activity.

The foregoing references describe compounds which may be structurally related to the compounds but are claimed to have broadly scattered and unrelated utilities. However, none of these compounds is stated to have antipsychotic properties such as those suggested for compounds of the invention.

More recently, but subsequent to our invention, Glennon et al., J. Med. Chem., 34, 3360–65 (December 1991) discloses compounds of formula:

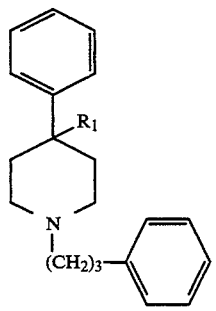

wherein R₁ is hydrogen or hyroxy.

These compounds are reportedly sigma receptor ligands.

SUMMARY OF THE INVENTION

The present invention provides useful compositions of the aforesaid class of substituted-piperidines having a novel combination of substituents attached to the 1- and the 4-positions of the piperidine ring.

It has been found that compounds of formula I hereinbelow including both known and novel species have sigma receptor activity and thus are useful in the treatment of central nervous system disorders, including psychiatric disorders.

Accordingly this invention relates to pharmaceutical compositions containing as the active ingredient thereof compounds of formula I

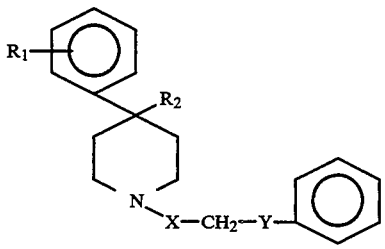

Formula I wherein
$R_1$ is hydrogen, hydroxy or lower-alkoxy;
$R_2$ is hydrogen, hydroxy, lower-alkanoyl, aroyl, lower-alkoxycarbonyl, lower-alkanoyloxy, carboxy or $CONR_3R_4$ where $R_3$ and $R_4$ are the same or different lower-alkyl or $R_3$ and $R_4$ together represent a lower-alkylene chain;
X is methylene or carbonyl;
Y is methylene, C=NOH, hydroxymethylene or carbonyl;
or their pharmaceutically acceptable acid addition salts.

The invention further relates to a method of treating central nervous system disorders, including psychiatric disorders, which comprises administering to a patient in need of such treatment an effective amount of a compound of formula I or a pharmaceutically acceptable acid addition salt thereof.

This invention also relates to novel compounds of formula I wherein
$R_1$ is hydrogen, lower-alkoxy, or hydroxy;
$R_2$ is hydrogen, hydroxyl, lower-alkanoyl, aroyl, carboxy, or $CONR_3R_4$ where $R_3$ and $R_4$ are the same or different lower-alkyl or $R_3$ and $R_4$ together represent a lower-alkylene chain;
X is carbonyl or methylene
Y is methylene
or their pharmaceutically acceptable acid addition salts, pharmaceutical compositions thereof, and a method of treatment of central nervous system disorders, including psychiatric disorders and psychoses.

DETAILED DESCRIPTION INCLUSIVE OF PREFERRED EMBODIMENTS

Noninteracting solvents are solvents that do not participate in the formation of product, which may include THF, ether, hexane, acetonitrile and the like.

Lower-alkanoyl means straight or branched alkanoyl having from 2 to about 5 carbons; for example acetyl, propionyl, butyryl, isobutyryl, valeryl and the like. Aroyl refers to benzoyl or benzoyl substituted with lower-alkoxy, hydroxy, halogen, cyano, trifluoromethyl or amino. Lower-alkanoyloxy means straight or branched alkanoyloxy with from 2 to about 4 carbon atoms, for example acetoxy, propionyloxy, isobutyryloxy and the like. The term lower-alkylene refers to a straight or branched divalent hydrocarbon chain with from about three to six carbons, examples include 1,3-propylene, 1,4-butylene, 1,5-pentylene, 1,6-hexylene, 1,3-dimethyl-1,4-butylene and the like. Thus it will be understood that when $R_3$ and $R_4$ together are lower-alkylene, the group $NR_3R_4$ represents a saturated heterocyclic substituent such as azetidinyl, pyrrolidinyl, piperidinyl and the like.

Lower-alkyl refers to a straight or branched hydrocarbon radical with from 1 to about 4 carbons, such as methyl, ethyl, propyl, isopropyl, butyl, sec-butyl, and the like. Lower-alkoxy refers to straight or branched alkoxy radical with from 1 to about 4 carbons such as methoxy, ethoxy, propoxy, isopropoxy, butoxy, sec-butoxy and the like. Lower-alkoxycarbonyl refers to such groups, straight or branched, having 2 to about 6 carbons such as methoxycarbonyl, ethoxycarbonyl, propoxycarbonyl, pentyloxycarbonyl and the like.

Novel compounds of formula I wherein Y is methylene are prepared by three general methods, depending upon their functionality;

a.) Compounds where X is CO;

An appropriately substituted 4-($R_1$-phenyl)-4-$R_2$-piperidine is reacted with 3-phenylpropionylhalide in the presence of an acid acceptor, for example an organic amine, between −50° C. and the boiling point of the reaction mixture yielding a 1-(3-phenylpropionyl)4-($R_1$-phenyl)-4-$R_2$ piperidine) of formula I. In cases where $R_1$ or $R_2$ are hydroxy, a preferred method reduces the reaction temperature to allow preferential formation of the amide leaving the hydroxyl free.

b.) Compounds where X is $CH_2$;

An appropriately substituted 4-($R_1$-phenyl)-4-$R_2$-piperidine is reacted with 3-phenylpropyl-Z, wherein Z is chloride, bromide, iodide, tosylate, or other good leaving group, in the presence of an acid acceptor, for example, n-butanol with sodium carbonate, at a temperature from −50° C. to the boiling point of the reaction mixture. In cases where $R_1$ or $R_2$ is hydroxy, it is preferred to use as a starting material a compound having $R_1$ or $R_2$ as lower-alkoxy which is cleaved in a final step by conventional methods well known in the art, for example with HBr or $BBr_3$, giving 4-($R_1$-phenyl)-4-$R_2$-1-(3-phenyl propyl)-piperidine of formula I.

c.) Compounds where $R_2$ is $CONR_3R_4$;

The appropriate 1-(3-phenylpropionyl) or 1-3-phenylpropyl)-4-($R_1$-phenyl)-4-piperidine carboxylic acid is prepared as described above, then the amide is prepared from this carboxylic acid by conventional means, for example treatment with an appropriate secondary amine, $R_3R_4NH$, in the presence of pyridine and benzenesulfonyl chloride at a temperature from ambient to the boiling point of the reaction mixture yielding compounds of formula I.

Starting materials for synthesis of compounds of formula I are commercially available, known or belong to families of known compounds and are prepared by methods well known in the art.

The compounds of the invention are sufficiently basic to form acid-addition salts, and are useful both in the free base form and the form of acid-addition salts, and both forms are within the purview of the invention. The acid-addition salts are in some cases a more convenient form for use, and in practice the use of the salt inherently amounts to the use of the base form. The acids which can be used to prepare the acid-addition salts include preferably those which produce, when combined with the free base, medicinally acceptable salts, that is, sales whose anions are relatively innocuous to the animal organism in medicinal doses of the salts so that the beneficial properties inherent in the free base are not vitiated by side effects ascribable to the anions.

Examples of appropriate acid-addition salts include but are not limited to the hydrochloride, hydrobromide, sulfate, acid sulfate, maleate, citrate, tartrate, methanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are prefered, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance and mass spectroscopy. The course of the reactions and the identity and homogeneity of the products were assessed by thin layer chromatography (TLC) or gas-liquid chromatography (GLC).

The following examples will further illustrate the invention without, however, limiting it thereto.

All reactions are performed under nitrogen atmosphere and in dried solvents unless otherwise specified hereinbelow.

These examples are prepared from starting materials, which are commercially available, known or come from known families of compounds and are prepared by methods well known in the art.

EXAMPLE 1

4-Phenyl-4-hyroxy-1-(3-phenylpropionyl) piperidine (Formula I: $R_1$=Hydrogen, $R_2$=OH, X=CO, Y=$CH_2$)

12.4 g 4-phenyl-4-piperidinol was taken up in chloroform. To this solution was added 15 ml triethylamine, then the solution was cooled in an ice bath and 11.8 g of 3-phenylpropionyl chloride, dissolved in 50 ml chloroform was added dropwise. The reaction mixture was allowed to stir for 1 hour. The chloroform phase was extracted with 100 ml each of 6N HCl, 3N HCl, water and 15% sodium bicarbonate, and then dried over magnesium sulfate and concentrated in vacuo. The resulting dried material was recrystallized from hot ethyl acetate, yielding 14.95 g of product, melting point 124°–125° C.

EXAMPLE 2

4-Phenyl-1-(3-phenylpropyl)-4-(1-pyrrolidinylcarbonyl)piperidine (Formula I $R_1$=Hydrogen,

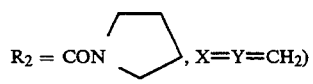

$R_2$ = CON, X=Y=$CH_2$)

a) 9.3 g Ethyl 1-(3-phenylpropyl)-4-phenyl-4-piperidine-carboxylate (Formula I: $R_1$=hydrogen, $R_2$=COOEt, X=Y=$CH_2$), prepared according to the procedure described in U.S. Pat. No. 2,914,532, incorporated herein by reference, was taken up in 35 ml water and 12 ml ethanol with 2.3 g sodium hydroxide, then refluxed for 24 hours and stirred at room temperature for the next two days. The product mixture was poured into water, the solution was acidified with acetic acid, and a precipitate appeared. The precipitate was washed well with water. The product was recrystallized from 4 liters of water and was washed with water, ethanol and ether, yielding 4-phenyl-1-(3-phenylpropyl)-4-piperidinecarboxylic acid, as a white powder, which was used without further purification in the next preparation.

b) 6 g (18.5 mmol) of the acid of example 2a and 0.7 g pyrrolidine were combined in 10 ml pyridine. 1.76 g (10 mmol) benzene sulfonyl chloride was added and the reaction mixture stirred for an hour. To the resulting solution 2.5 g sodium hydroxide and 1 g $NaHSO_3$ was added, and the side of the vessel scratched until the solid formed. The solid was taken up in ether, filtered and treated with ethereal HCl. The product was recrystallized from chloroform/ethylacetate to give 1.4 g of the piperidine carboxamide of formula I, melting point 198°–200° C., as the HCl salt.

EXAMPLE 3

Preparation of 4-(3-hydroxyphenyl)-1-(3-phenyl-propyl)piperidine (Formula I $R_1$=3-OH, $R_2$=Hydrogen, X=Y=$CH_2$)

a.) 8.5 g of 4-(3-methoxyphenyl) piperidine, 8.2 g of potassium carbonate and 10.3 g of 1-bromo-3-phenyl-propane were refluxed in 80 ml acetonitrile for 25 hours. The hot reaction mixture was filtered and the solids washed twice with hot acetonitrile. The filtrate was then concentrated in vacuo, leaving 15.4 g of residue. Water and 10% NaOH were added to the residue and the mixture was extracted twice with ether. The ether portions were combined and washed with brine, dried over magnesium sulfate, and concentrated in vacuo to an oil. The oil was taken up in 100 ml pentane and filtered through a plug of silica and concentrated in vacuo. The resulting oil was taken up in acetone and treated with ethereal HCl, yielding a precipitate. When air dried, 11.1 g of 4-(3-methoxyphenyl)- 1-(3-phenylpropyl)piperidine hydrochloride, melting point 218°–220° C., was obtained.

b.) 6.7 g 4-(3-methoxyphenyl)-1-( 3-phenylpropyl)-piperidine hydrochloride was refluxed with 80 ml 48% HBr for an hour. The products were cooled, the aqueous layer decanted and concentrated in vacuo. The resulting residue and insolubles were treated with excess saturated sodium bicarbonate and extracted with methylene chloride twice. The methylene chloride layer was washed twice with saturated bicarbonate and dried over magnesium sulfate and concentrated in vacuo. The resulting viscous oil was taken up in 50 ml acetone and HCl was added, resulting in precipitation. The precipitate was filtered off affording 8.6 g of crude product. The product was recrystallized from 110 ml absolute ethanol and 50 ml ether, yielding 4-(3-hydroxyphenyl)-1-(3-phenylpropyl)piperidine hydrochloride, melting point 211°–213° C.

EXAMPLE 4

Preparation of
4-benzoyl-4-phenyl-1-(3-phenylpropyl)piperidine
(Formula I $R_1$=hydrogen, $R_2$=benzoyl, $X=Y=CH_2$)

3 g 4-benzoyl-4-phenylpiperidine was taken up in 200 ml n-butanol with 1.5 ml 1-bromo-3-phenylpropane and 10 g sodium carbonate, and refluxed for 4 hours. The resulting mixture was filtered and the filtrate concentrated in vacuo, taken up in ethyl acetate and washed with water. The ethyl acetate layer was dried over potassium carbonate and eluted through a short silica plug with 1:1 hexane/ethyl acetate. The eluted product was concentrated to dryness overnight, giving 3.14 g of product, melting point: 185°–186° C.

EXAMPLE 5

4-Phenyl-1-(3-phenylpropyl)-4-propionylpiperidine
(Formula I $R_1$=Hydrogen, $R_2$=COEt, $X=Y=CH_2$)

6 g 4-phenyl-4-propionylpiperidine and 3.6 ml 1-bromo-3-phenylpropane was refluxed in 500 ml n-butanol with 10 g sodium carbonate for 16 hours. The reaction mixture was filtered through a silica plug and concentrated in vacuo. The residue was taken up in ethyl acetate and washed with water, then saturated brine and dried over potassium carbonate. The solution was concentrated in vacuo, 8 g of the residue was taken up in 150 ml acetonitrile and heated with 2.5 g fumaric acid. The resulting precipitate was collected by filtration, giving 3 g 4-phenyl-1-(3-phenylpropyl)-4-propionylpiperidine as the fumarate salt, melting point 136°–138° C.

EXAMPLE 6

4-Phenyl-1-(3-oximino-3-phenylpropyl)-4-propionoxypiperidine (Formula I: $R_1$=hydrogen, $R_2$=OCOEt, $X=CH_2$ $Y=CNOH$), was prepared as described in U.S. Pat. No. 3,217,009 incorporated herein by reference.

EXAMPLE 7

Ethyl
4-Phenyl-1-(3-phenylpropyl)-4-piperidinecarboxylate
(Formula I: $R_1$=hydrogen, $R_2$=COOEt, $X=Y=CH_2$), was prepared as described in U.S. Pat. No. 2,914,332 incorporated herein by reference.

BIOLOGICAL TEST RESULTS

In standard biological test procedures, representative examples of the compounds of the invention have been found to bind with high affinity to sigma receptors, and are thus useful in the treatment of central nervous system disorders such as psychoses, dystonias, dyskinesias, Parkinson's syndrome, Huntington's chorea, Tourette syndrome, and the like, especially psychoses, e.g., schizophrenic psychoses, manic depressive psychoses and the like.

The sigma receptor binding activity of representative compounds of the inventions was demonstrated by a procedure essentially described by Hudkins and DeHaven-Hudkins, Life Science 1991, 49(17), 1229–1235.

Brain tissue was prepared from male Hartley guinea pigs (Hazelton Labs, Denver, Pa.) which were anesthetized with $CO_2$ and sacrificed by decapitation. All animal care and use procedures were in accord with the "Guide for the Care and Use of Laboratory Animals" (NIH Publ. No. 86-23, 1985). Homogenization was performed in 10 volumes (wt/vol) of 0.32M sucrose with a Brinkmann Polytron at setting 5, 30 sec. The homogenate was centrifuged at 900×g for 10 min at 4° C., and the supernatant was collected and centrifuged at 22,000×g for 20 min at 4° C. The pellet was resuspended in 10 volumes of Tris-HCl buffer (50 mM, pH 7.4), incubated at 37° C. for 30 min and centrifuged at 22,000×g for 20 min at 4° C. Following this, the pellet was resuspended in Tris buffer and frozen in 5–10 mL aliquots corresponding to a tissue concentration of 100 mg/mL at −70° C. Binding characteristics of the membranes were stable for at least one month when stored at −70° C.

On the day of the assay, membrane aliquots were thawed, resuspended in fresh Tris buffer and stored on ice until use. Each assay tube contained 100 μL of [$^3$H](+)pentazocine at a final concentration of approximately 0.5 nM, [$^3$H]di(2-tolyl)-guanidine (DTG) at a final concentration of approximately 4 nM, 100 μL of various concentrations of the compounds of interest, 500 μL of the tissue suspension and 300 μL of buffer to a final assay volume of 1 mL and a final tissue concentration of approximately 8 mg/tube, corresponding to approximately 0.15 mg protein/tube. Nonspecific binding was defined by addition of a final concentration of 1 μM haloperidol to blank tubes for the [$^3$H](+)pentazocine assay or by addition at a final concentration of 10 μM haloperidol to blank tubes for [$^3$H] DTG assay. All tubes were incubated at 37° C. for 150 min ([$^3$H](+)pentazocine) or at 25° C. for 90 min ([$^3$H]DTG) before termination of the reaction by filtration over Whatman GF/B glass fiber filters that were presoaked in a solution of 0.5% polyethyleneimine for at lease 1 hr prior to use. Filters were washed with three 4 mL volumes of cold Tris-HCl buffer.

Following addition of scintillation cocktail, samples were allowed to equilibrate for at least 4 hr. The amount of bound radioactivity was determined by liquid scintillation spectrometry using a Beckman LS 5000 TA liquid scintillation counter with an efficiency for tritium of approximately 60%. The results are reported as a percent (%) inhibit ion of binding at 10 μM.

The following Table summarizes the results obtained from the testing of representative compounds of the invention.

Data obtained on the compounds in the di(2-tolyl)-guanidine (DTG) and d-pentazocine (+Pent) assays are expressed as a Ki value in nM. The number of determinations follow this value in parentheses.

| Example | DTG | + Pent |
| --- | --- | --- |
| 1 | 34392 (3) | — |
| 2a | 16.4 (3) | 1.74 (4) |
| 2b | 116 (2) | — |
| 3a | 2.21 (3) | — |
| 3b | 0.65 (3) | — |
| 4 | 22.1 (4) | 0.8 (4) |
| 5 | 9.1 (3) | 0.38 (3) |

-continued

| Example | DTG | + Pent |
|---------|---------|--------|
| 6 | 589 (4) | — |
| 7 | 88.9 (2) | — |

The compounds of the invention can be prepared for pharmaceutical use by conventional pharmaceutical procedures that are well known in the art; that is by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, per fuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion and like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound having the formula;

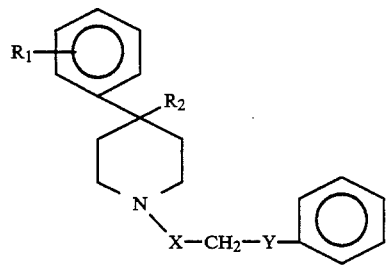

wherein;

$R_1$ is hydrogen, hydroxy or lower-alkoxy $R_2$ is hydrogen, hydroxy, lower-alkanoyl or aroyl, or $CONR_3R_4$; $R_3$ and $R_4$ are the same or different lower-alkyl or $R_3$ and $R_4$ together represent a lower-alkylene chain;

X is methylene;

or a pharmaceutically acceptable acid addition salt thereof.

2. A compound according to claim 1 wherein X is methylene, $R_2$ is hydrogen and $R_1$ is hydroxy or methoxy.

3. A compound according to claim 1 wherein X is methylene, $R_1$ is hydrogen, and $R_2$ is hydroxy, or $CONR_3R_4$; $R_3$ and $R_4$ are the same or different lower-alkyl or $R_3$ and $R_4$ together represent a lower-alkylene chain.

4. A compound according to claim 1, wherein X is methylene, $R_2$ is lower-alkanoyl or aroyl and $R_1$ is hydrogen.

5. A compound according to claim 1 wherein X is methylene, $R_1$ is hydrogen and $R_2$ is $CONR_3R_4$; $R_3$ and $R_4$ together represent a lower-alkylene chain.

6. A compound according to claim 1 selected from the group consisting of:
   4-phenyl-1-(3-phenylpropyl)-4-(1-pyrrolidinylcarbonyl)piperidine;
   4-benzoyl-4-phenyl-1-(3-phenylpropyl)piperidine;
   4-phenyl-4-propionyl-1-(3-phenylpropyl)piperidine;
   4-(3-methoxyphenyl)-1-(3-phenylpropyl)piperidine; and
   4-(3-hydroxyphenyl)-1-(3-phenylpropyl)piperidine.

7. A pharmaceutical composition for treating psychosis comprising a pharmaceutical carrier and, as an active component thereof, an antipsychotically effective amount of a compound according to claim 1.

8. A composition according to claim 7 where X is methylene, $R_1$ is hydrogen and $R_2$ is hydroxy, lower alkanoyl, aroyl, or $CONR_3R_4$.

9. A composition according to claim 8 wherein X is methylene and $R_2$ is lower alkanoyl or aroyl.

10. A composition according to claim 8 wherein X is methylene and $R_2$ is $CONR_3R_4$; and $R_3$ and $R_4$ together represent a lower alkylene chain.

11. A composition according to claim 7 wherein X is methylene, $R_2$ is hydrogen and $R_1$ is hydroxy or methoxy.

12. A method for the treatment of psychosis, comprising administering to a patient in need of such treatment a medicament containing an antipsychotically effective amount of a compound according to claim 1.

13. A method according to claim 12, wherein X is methylene, $R_1$ is hydrogen and $R_2$ is hydroxy, lower alkanoyl or aroyl, or $CONR_3R_4$; $R_3$ and $R_4$ are the same or different lower-alkyl or $R_3$ and $R_4$ together represent a lower-alkylene chain.

14. A method according to claim 13, wherein X and Y are methylene and $R_2$ is lower-alkanoyl or aroyl, $R_1$ is hydrogen.

15. A method according to claim 13 wherein X and Y are methylene, $R_1$ is hydrogen, and $R_2$ is $CONR_3R_4$; $R_3$ and $R_4$ together represent a lower-alkylene chain.

16. A method according to claim 12, wherein X is methylene, $R_2$ is hydrogen and $R_1$ is hydroxy or methoxy.

* * * * *